(12) United States Patent
Okajima et al.

(10) Patent No.: US 7,875,267 B2
(45) Date of Patent: Jan. 25, 2011

(54) BODY CAVITY CLEANING AGENT

(75) Inventors: Takao Okajima, Tokyo (JP); Susumu Fujinami, Tokyo (JP)

(73) Assignee: KAO Corporation, Tokyo (JP)

( * ) Notice: Subject to any disclaimer, the term of this patent is extended or adjusted under 35 U.S.C. 154(b) by 0 days.

(21) Appl. No.: 12/748,677

(22) Filed: Mar. 29, 2010

(65) Prior Publication Data

US 2010/0180907 A1 Jul. 22, 2010

Related U.S. Application Data

(62) Division of application No. 10/553,783, filed as application No. PCT/JP2004/005937 on Apr. 23, 2004, now abandoned.

(30) Foreign Application Priority Data

Apr. 24, 2003 (JP) ............................. 2003-120567
Mar. 31, 2004 (JP) ............................. 2004-107345

(51) Int. Cl.
*A61Q 5/12* (2006.01)
*A61K 7/50* (2006.01)
*A47K 7/00* (2006.01)

(52) U.S. Cl. .................................................. 424/70.12
(58) Field of Classification Search ........................ None
See application file for complete search history.

(56) References Cited

U.S. PATENT DOCUMENTS

| | | | |
|---|---|---|---|
| 2,914,442 A | 11/1959 | Halpern | |
| 4,412,096 A | 10/1983 | Edgerton et al. | |
| 4,661,099 A * | 4/1987 | von Bittera et al. | ......... 604/290 |
| 4,714,739 A | 12/1987 | Arkles et al. | |
| 4,891,400 A | 1/1990 | Schwabe et al. | |
| 5,360,858 A | 11/1994 | Fujiki et al. | |
| 5,484,871 A | 1/1996 | Stepp | |
| 5,556,914 A | 9/1996 | Colas et al. | |
| 5,674,966 A | 10/1997 | McDermott et al. | |
| 5,744,199 A | 4/1998 | Joffre et al. | |
| 6,254,811 B1 | 7/2001 | Finger et al. | |
| 6,328,564 B1 | 12/2001 | Thurow | |
| 6,417,179 B1 | 7/2002 | Burkhart et al. | |

FOREIGN PATENT DOCUMENTS

DE 29919149 * 4/2001

(Continued)

OTHER PUBLICATIONS

"Newly Edited Dentistry Engineering" published Apr. 1987 by Gakken Shoin Kabushiki Kaisya.

(Continued)

*Primary Examiner*—Andrew D Kosar
*Assistant Examiner*—Lori Mattison
(74) *Attorney, Agent, or Firm*—Oblon, Spivak, McClelland, Maier & Neustadt, L.L.P.

(57) ABSTRACT

A body cavity cleansing agent of the present invention is either poured into or applied to a navel cavity (N) or an ear hole and solidifies after a specified period of time, and the cleansing agent takes a form that can be removed from the navel cavity (N) or the ear hole together with dirt in the navel cavity (N) or the ear hole.

4 Claims, 8 Drawing Sheets

FOREIGN PATENT DOCUMENTS

| | | |
|---|---|---|
| JP | 09-205699 | 8/1997 |
| JP | 9-511231 | 11/1997 |
| JP | 2000-229045 | 8/2000 |
| JP | 2002-34830 | 2/2002 |
| WO | WO 99/12582 A2 | 3/1999 |
| WO | WO 99/12582 A3 | 3/1999 |
| WO | WO 03/020358 A1 | 3/2003 |

OTHER PUBLICATIONS

Introduction to Polymer Science and Technology: An SPE Texbook (Ed. H. Kaufman, John Willey & Sons, New York) pp. 184-187 (1977).

Polymers in Aqueous Media, Advances in Chemistry Series (Ed. E. Glass, American Chemical Soc., Washington, DC), pp. 417-420 (1989).

"Idea.com: 'Bellybutton Clean' sales page" (online) of COGIT Co.; HP division, COGIT Co.: URL http://www.rakuten.co.jp/cogit/390263/452459/ on internet; searched on Apr. 1, 2003.

Plant Compounds and Resin in Restance Mechanisms. http://www.chemical-ecology-net/papers/bb54.htm. Accessed Aug. 16, 2009.

Questions.Abilene Speech & Hearing Center. © 2002. http://www.abilinehearing.com/questions.htm. Accessed Oct. 16, 2008.

Protocol for Earmold Impressions. LT Andy Hayes. http://www-mcphc.med.navy.mil/occmed/ProtocolForTakingAnEarmoldImpressionAndyHayes.doc. Assessed Oct. 16, 2008.

* cited by examiner

BODY CAVITY CLEANING AGENT

TECHNICAL FIELD

The present invention relates to a body cavity cleansing agent used for removing dirt (such as bellybutton lint or ear wax and the like) from a body cavity such as the navel cavity or the ear hole and the like, a body cavity cleansing method using this cleansing agent, and a navel cavity opener used when pouring the body cavity cleansing agent into the navel cavity.

BACKGROUND ART

In recent years, those fashions with an exposed bellybutton or with a pierced bellybutton have become common, and also there is a trend to wear a swimsuit as outerwear, there are more opportunities to expose one's bellybutton. Bellybutton lint accumulated in the navel cavity is not only unpleasant to look at, but also generates odor because of bacteria growth in the navel cavity. Therefore, bellybutton lint removal (bellybutton cleansing) is performed for the purposes of improving the appearance and preventing odor of the bellybutton.

Commonly, bellybutton lint removal is performed by scratching with a fingernail or scraping with an oil-applied swab See IDS filed on Jan. 20, 2006 in U.S. application Ser. No. 10/553,783. However, scratching with a fingernail or scraping with a swab can easily hurt the inner surface of the navel cavity. Moreover, it gives a stimulus to the abdominal membrane under the bottom of the navel cavity, which can lead to abdominal pain.

Meanwhile, conventionally, ear wax removal (ear cleansing) is performed using an earpick or a swab. However, with the ear cleansing using an earpick or the like, ear wax is not completely removed as a result of avoiding damage to a deeper part of the ear hole, and sometimes it is the case that ear wax is pushed into the deeper part of the ear hole and becomes harder to be scraped out, and also, the inner surface of the ear hole can easily get hurt.

DISCLOSURE OF THE INVENTION

Accordingly, an object of the present invention is to provide a body cavity cleansing agent with which dirt such as bellybutton lint or ear wax and the like can be easily removed without hurting the inner surface of the navel cavity or the ear hole and the like, a body cavity cleansing method using this cleansing agent, and a navel cavity opener used when pouring the body cavity cleansing agent into the navel cavity.

To achieve the above object, the present invention provides a body cavity cleansing agent which is either poured into or applied to a navel cavity or an ear hole and solidifies after a specified period of time, and which takes a form that can be removed from the navel cavity or the ear hole together with dirt in the navel cavity or the ear hole.

The present invention also provides a body cavity cleansing method wherein the above body cavity cleansing agent is either poured into or applied to a navel cavity or an ear hole, and after the body cavity cleansing agent has solidified, this solid material is removed from the navel cavity or the ear hole together with dirt in the navel cavity or the ear hole.

The present invention also provides a navel cavity opener for stretching and opening a navel cavity so as to allow the above body cavity cleansing agent to be poured into the navel cavity, including a tubular part, a flange formed such as to extend from an outer circumferential surface of the tubular part, and a plurality of fins extending from the outer circumferential surface of the tubular part at a predetermined interval, wherein the tubular part is provided with a cleansing agent injection port at an upper end thereof, a cleansing agent discharge port that communicates with the cleansing agent injection port is provided on a lower end side of the tubular part relative to the flange, and the fins extend from the lower end of the tubular part toward the flange such that their height from the tubular part increases gradually.

DETAILED DESCRIPTION OF THE INVENTION

One preferred embodiment of the body cavity cleansing agent of the present invention will be hereinafter described. FIG. 3(a) to FIG. 3(d) and FIG. 4(a) to FIG. 4(e), which will be described later, will also be referred to in the description of how the body cavity cleansing agent is poured into a navel cavity and solidifies. It should be noted that the body cavity cleansing agent of the present invention is prepared as a composition having fluidity before use or at least during use. Therefore a term "fluid composition" in the following description also refers to the body cavity cleansing agent of the present invention.

Figure 3A:
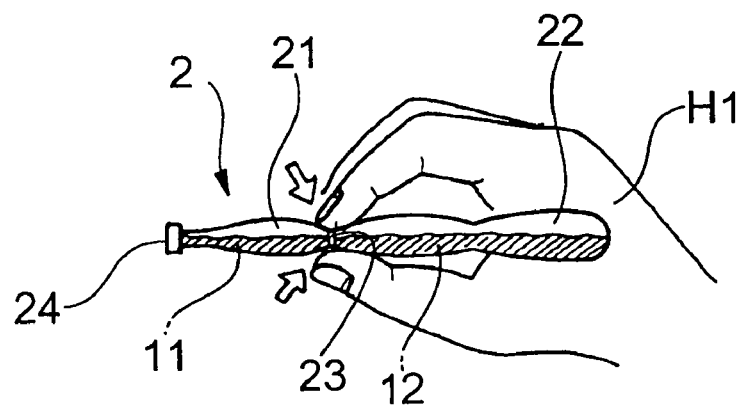
FIG. 3(a), FIG. 3(b), FIG. 3(c), and FIG. 3(d) are diagrams showing the former half of the process steps of one embodiment of the body cavity cleansing method (bellybutton cleansing) of the present invention.
Figure 3B:
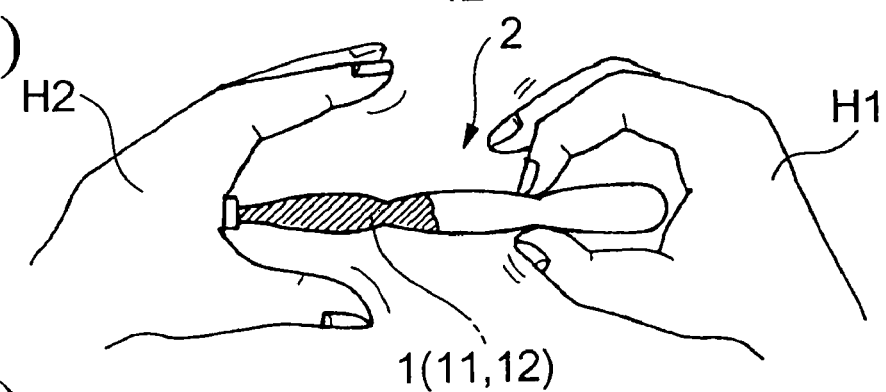
Figure 3C:
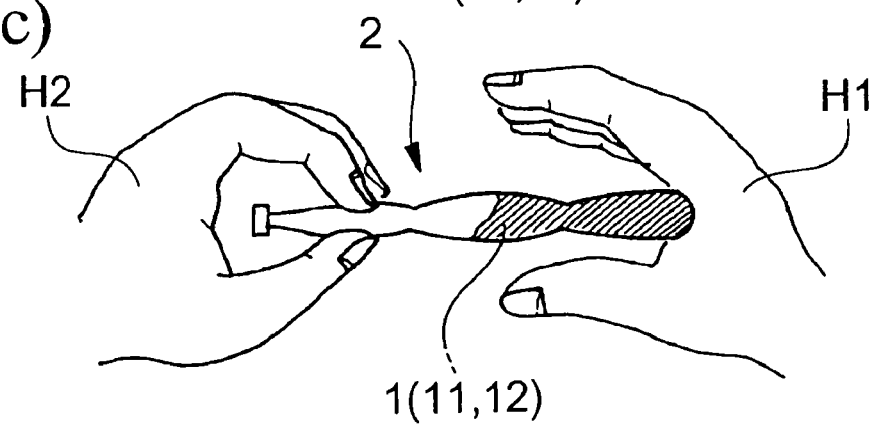
Figure 3D:
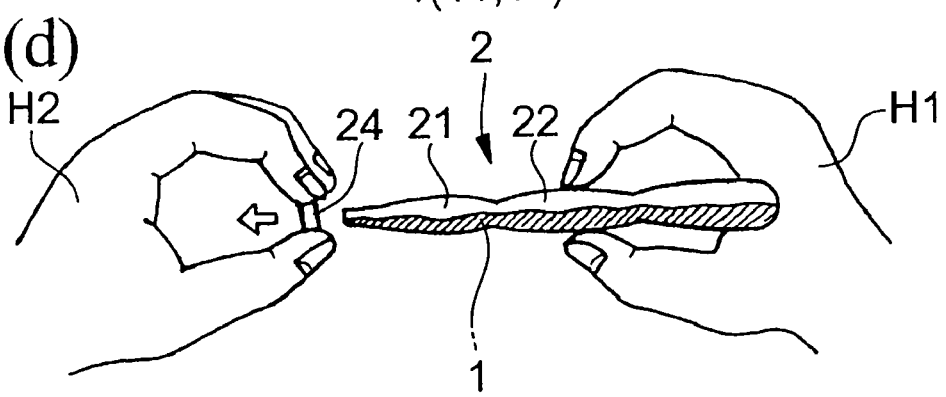
Figure 4A:
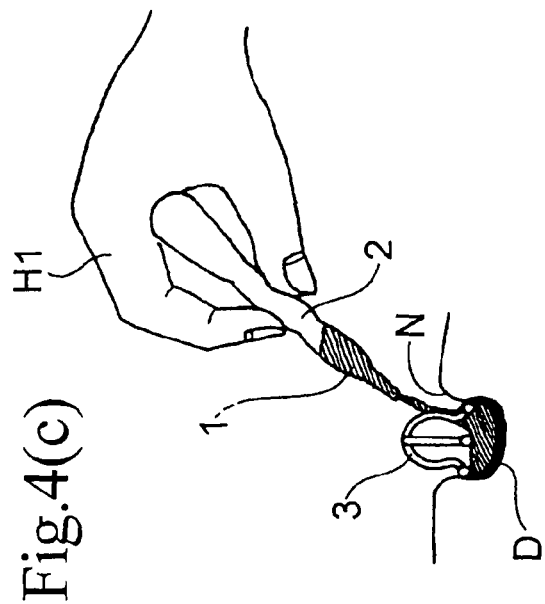
FIG. 4(a), FIG. 4(b), FIG. 4(c), FIG. 4(d), and FIG. 4(e) are diagrams showing the latter half of the process steps of one embodiment of the body cavity cleansing method (bellybutton cleansing) of the present invention.
Figure 4B:
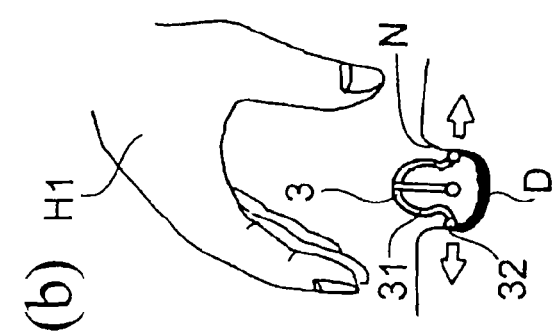
Figure 4C:
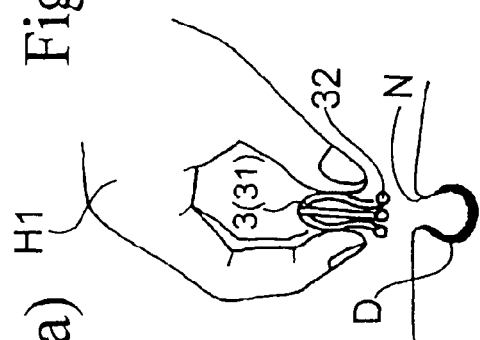
Figure 4D:
Figure 4E:
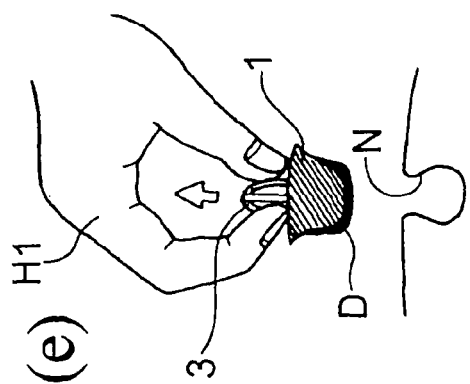

The body cavity cleansing agent 1 of the present embodiment is a fluid composition that can be poured into a body's navel cavity N prepared as shown in FIG. 3(a) to FIG. 3(d), and it solidifies into a gel-like or rubber-like state after a specified period of time after it has been poured into the navel cavity N as shown in FIG. 4(c). After the body cavity cleansing agent 1 of the present embodiment has solidified in the navel cavity N as shown in FIG. 4(d), it takes a form that can be removed from the navel cavity N together with dirt (bellybutton lint) D in the navel cavity N as shown in FIG. 4(e).

For example, the body cavity cleansing agent of the present embodiment is composed of a silicone rubber composition having two-component hardening system, including a first agent and a second agent, the first agent being a reactive silicone base composed mainly of diorganopolysiloxane and the second agent being a curing agent base containing a crosslinking agent. Such two-component composition may further contain a curing catalyst either in the first agent or the second agent. The diorganopolysiloxane used for the first agent of this two-component hardening system silicone rubber composition may be a hydroxylated diorganopolysiloxane containing at least two hydroxyl groups in the molecule, or a vinyl-terminated diorganopolysiloxane containing at least two vinyl groups in the molecule. The crosslinking agent and the curing catalyst are selected in accordance with which of these is used.

The hydroxylated diorganopolysiloxane, in particular, is preferably a hydroxylated dimethylpolysiloxane containing a hydroxyl group at each end, because the material cures quickly and causes no skin irritation. The crosslinking agent in the composition of the present invention, when a hydroxylated diorganopolysiloxane is used for the first agent, is preferably an alkoxysilane containing at least two alkoxy groups in the molecule, such as methyl-trimethoxysilane, tetraethylsilicate, tetrapropylsilicate, or the like. The curing catalyst, in this case, is preferably carboxylate metal salt, an amine compound, or amine hydrochloride, such as dibutyltin dilaurate, dibutyltin acetate, dibutyltin dioctanoate, dioctyltin dilaurate, or the like.

The vinyl-terminated diorganopolysiloxane, in particular, is preferably a vinyl-terminated dimethylpolysiloxane containing a vinyl group at each end, because the material cures quickly and causes no skin irritation. The crosslinking agent, when a vinyl-terminated diorganopolysiloxane is used for the first agent, is preferably a hydrogenated diorganopolysiloxane containing at least two Si—H groups in the molecule. The curing catalyst, in this case, is preferably a platinum compound, such as chloroplatinic acid, platinum black, platinum asbestos, silica-gel-supported platinum, platinum activated carbon, potassium chloroplatinate, or the like.

Preferably, the silicone rubber composition having two-component hardening system of the present embodiment contains 0.1 to 30 weight parts of the crosslinking agent and 0.001 to 10 weight parts of the curing catalyst, relative to 100 weight parts of the diorganopolysiloxane. The composition ratio is suitably selected in accordance with the kind of each component and the purpose of use.

The body cavity cleansing agent of the present invention is not limited to the above embodiment and may be any form as long as the agents are either poured into or applied to a navel cavity or an ear hole and solidify after a specified period of time, and they can take a form that can be removed from the navel cavity or the ear hole together with dirt in the navel cavity or the ear hole. For example, silicone rubber compositions having two-component hardening system, or a combination of sodium alginate and a calcium compound may be used. Among them, a silicone rubber composition having two-component hardening system is preferably used.

The body cavity cleansing agent of the present invention may further include, either alone or in combination, one of a sterilizer, a lubricant, fragrance, a surfactant, a polyol, a fiber material, powder, and an oil component, in order to further improve its usability. For the sterilizer, triclosan, silver zeolite (Sinanen Zeomic), and the like may be used; for the lubricant, propylene glycol, polyethylene glycol, and the like may be used; and for the fragrance, essential oils such as tee tree or grapefruit oils may be used.

Furthermore, the body cavity cleansing agent of the present invention is preferably harmless to the body because of its purpose of use. For the bellybutton cleansing, the fluid composition just before being poured or applied preferably has a viscosity of not more than 3,000 mPa·s. For the ear cleansing, the fluid composition preferably has such a viscosity that it does not flow into the middle ear after it is poured or applied and does not completely plug the ear hole. Specifically, the viscosity is preferably from 1,000 to 3,000 mPa·s.

The body cavity cleansing agent of the present invention is a curable composition which is mixed and prepared just before use and poured into or applied to the navel cavity or the ear hole while it still has sufficient fluidity, and solidifies after a specified period of time. The solidifying (curing) time (which is time required until the composition sets and can be removed as a solid material) is preferably from 0.5 to 20 minutes, and more preferably from 3 to 15 minutes, in terms of work efficiency. The composition preferably solidifies into a gel-like or rubber-like state so that the solidified composition is easy to remove from the navel cavity or the ear hole. The composition may contain menthol so as to give a feeling of coolness when the composition is applied to the navel cavity or the ear hole. Alternatively, the composition may contain red pepper extract so as to give a feeling of warmness.

Next, a preferred embodiment of the body cavity cleansing method of the present invention will be described with reference to FIG. 3(*a*) to FIG. 3(*d*) and FIG. 4(*a*) to FIG. 4(*e*). The body cavity cleansing method of the present embodiment uses the body cavity cleansing agent of the above embodiment for the cleansing of the navel cavity (bellybutton cleansing), wherein the above body cavity cleansing agent (fluid composition) is poured into the navel cavity N, and after the body cavity cleansing agent has solidified, this solid material is removed from the navel cavity N together with dirt (bellybutton lint) D in the navel cavity N.

Figure 1:
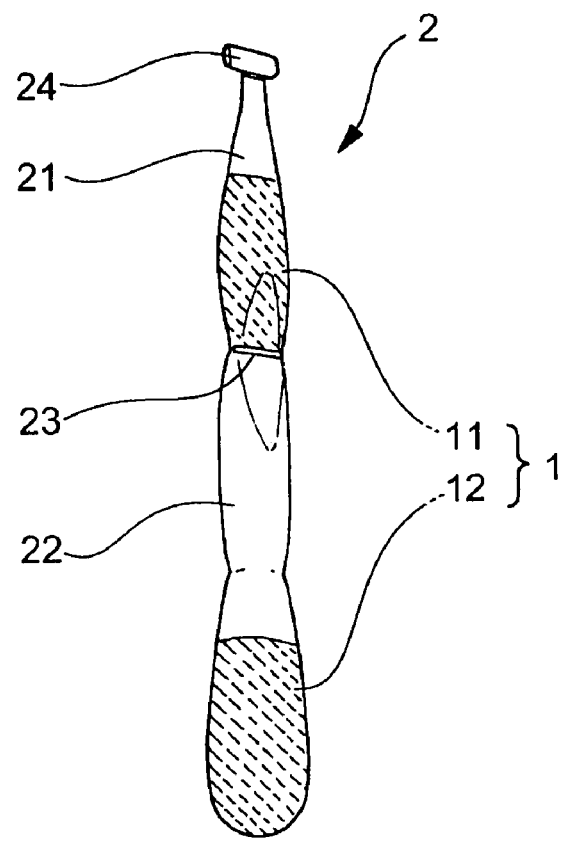
FIG. 1 is a perspective view showing a container/injector case for containing the body cavity cleansing agent of the present embodiment.

Before giving a description of the body cavity cleansing method of the present embodiment, a container/injector case 2 for injecting the body cavity cleansing agent of the above embodiment into the navel cavity and an opener 3 for stretching and opening the opening of the navel cavity will be described with reference to FIG. 1 and FIG. 2. The container/injector case 2 is divided into a first container part 21 and a second container part 22 as shown in FIG. 1, the first container part 21 containing the first agent 11 of the body cavity cleansing agent 1 of the above embodiment in a sealed manner, and the second container part 22 containing the second agent 12 in a sealed manner.

A partition 23 is provided between the first container part 21 and the second container part 22 for separating them. This partition 23 breaks into two pieces when an appropriately large external force is applied from the outside, for example, when pressed between the fingers as shown in FIG. 3(*a*), so that the first container part 21 and the second container part 22 communicate with each other. The container/injector case 2 is provided with a closure piece 24 at one terminal end on the side of the first container part 21. When the closure piece 24 is cut off from the first container part 21, the terminal end side of the first container part 21 opens.

Figure 2:
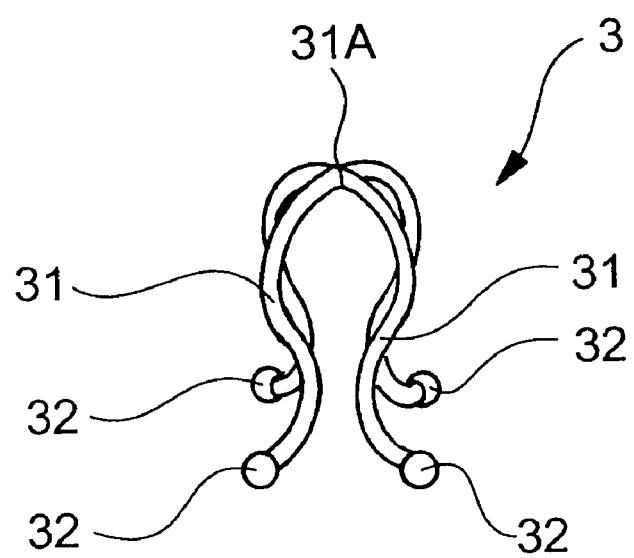
FIG. 2 is a perspective view showing one form of an opener for stretching and opening the opening of a navel cavity.

The opener 3 has a shape formed by two Ω-shaped members 31 bonded together with their tops 31A crossed at right angles when viewed from above, as shown in FIG. 2. The pair of terminal ends 32 and 32 of the Ω-shaped member 31 each has spherical parts so as to avoid hurting the opening of the navel cavity N when stretching and opening the opening with these terminal ends 32.

The opener 3 is made of a resilient member having resiliency such as synthetic resin, metal, and the like, and therefore, after the Ω-shaped members 31 are pressed so that the pairs of the terminal ends 32 come closer as shown in FIG. 4(*a*), the Ω-shaped members 31 return to their original state when the pressure is removed. The opener 3 has such a size that when the terminal ends 32 are pressed toward each other, these terminal ends 32 can be placed in the opening of a navel cavity N that is not fully opened. Then, the size is such that when the pressure is removed, the opening of the navel cavity N is stretched and opened to an appropriate size with the terminal ends 32. This opener 3 need not be used if the navel cavity is opened enough to allow the body cavity cleansing agent 1 to be poured in.

Next, the body cavity cleansing method (bellybutton cleansing) of the present embodiment using the above container/injector case 2 and the opener 3 will be described with reference to FIG. 3(a) to FIG. 3(d) and FIG. 4(a) to FIG. 4(e). The navel cavity N to be cleaned has a shape narrowing toward the opening as shown in FIG. 4(a), a shape that does not allow, as it is, the body cavity cleansing agent 1 contained in the container/injector case 2 to be smoothly poured in.

First, the container/injector case 2 is held, for example, by a right hand H1 as shown in FIG. 3(a), and the partition 23 is crushed with fingers. As a result, the first container part 21 and the second container part 22 of the container/injector case 2 communicate with each other, and the first agent 11 and the second agent 12 make contact with each other. Then, as shown in FIG. 3(b) and FIG. 3(c), the first agent 11 and the second agent 12 are mixed well inside the first container part 21 and the second container part 22 communicating with each other. As a result, a fluid composition 1 that can be poured into the navel cavity is obtained. After mixing the first agent and the second agent well enough, the closure piece 24 is cut off from the container/injector case 2 by pulling, folding, or twisting, as shown in FIG. 3(d). As a result, the fluid composition 1 mixed inside the container/injector case 2 communicates with the outside.

Prior to mixing of the first agent and the second agent, the opening of the navel cavity is stretched and opened in advance, using the opener 3, as described below. The opener 3 is picked by the hand H1, and the Ω-shaped members 31 are pressed from the sides to press together the terminal ends 32, as shown in FIG. 4(a). In this state, the terminal ends 32 of the Ω-shaped members 31 are inserted into the opening of the navel cavity N and set in place. Then, as shown in FIG. 4(b), when the pressure to the Ω-shaped members 31 is removed, the Ω-shaped members 31 attempt to restore to their original shape (in which the terminal ends 32 are separated from each other). The opening of the navel cavity N is thus stretched and opened with the terminal ends 32 by this restoring force of the Ω-shaped members 31.

With the opening of the navel cavity N stretched and opened by the Ω-shaped members 31 as described above, the fluid composition 1 mixed in the container/injector case 2 is poured into the navel cavity N until the terminal ends 32 of the opener 3 are submerged, as shown in FIG. 4(c) and FIG. 4(d). The fluid composition 1 is then left standing for a specified period of time in this state, until it solidifies (cures). The solidifying time differs depending on the composition and properties of the body cavity cleansing agent 1, or the amount poured into the navel cavity N. When the body cavity cleansing agent (fluid composition) 1 has solidified, the gel-like or rubber-like composition 1 is unified with the opener 3.

After that, as shown in FIG. 4(e), the opener 3 is picked and pulled out from the navel cavity N together with the solidified body cavity cleansing agent 1. As a result, the bellybutton lint (dirt) D adhered around the bottom of the navel cavity N is removed from the navel cavity N together with the body cavity cleansing agent 1.

By thus performing the bellybutton cleansing in the mode shown through FIG. 3(a) to FIG. 3(d) and FIG. 4(a) to FIG. 4(e) using the body cavity cleansing agent 1 of the present embodiment, the bellybutton lint D is readily removed from the navel cavity N. In this process, there is no risk that the inner surface of the navel cavity N is hurt or a stimulus is given to the abdominal membrane as compared with the case where the bellybutton is scratched with a fingernail or scraped with a swab. By using the above-described opener 3, the opening of a navel cavity N that is not fully opened can be stretched and opened, and thus facilitating the pouring of the composition 1 thereinto. Also, the opener 3 makes the removal process easier, as the composition 1 accompanied by the bellybutton lint D can be removed from the navel cavity N together with the opener 3 by removing the opener 3 from the navel cavity N after the composition 1 has solidified. Moreover, as the bellybutton lint D is removed together with the composition 1, the removal effect is clearly visible, which gives a feeling of the effect of the cleansing process. If the navel cavity is primarily opened enough to allow the body cavity cleansing agent to be poured in, the composition may be directly poured into the navel cavity without using the opener.

The opener, as long as it can stretch and open the opening of the navel cavity and in that state allow the body cavity cleansing agent of the present invention to be poured into or applied to the navel cavity, is not limited to the form shown in FIG. 2. A preferred form of the opener would have a structure that can stretch and open the navel cavity gradually as it is inserted into the navel cavity. For example, an opener 30 shown in FIG. 5, an opener 30' shown in FIG. 6, and an opener 30" shown in FIG. 7 and FIG. 8(a) to FIG. 8(d) may be used.

Figure 5:
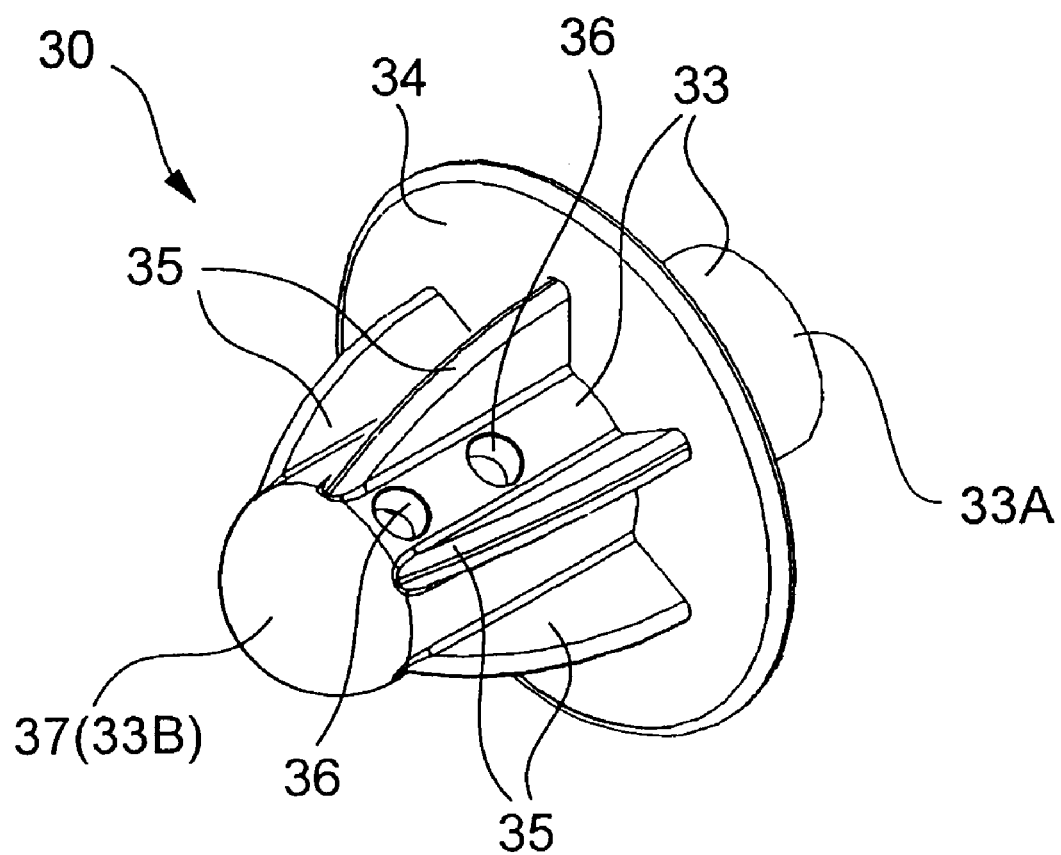
FIG. 5 is a perspective view showing one embodiment of the navel cavity opener of the present invention for stretching and opening the opening of a navel cavity.

The opener 30 shown in FIG. 5 includes a cylindrical tubular part 33, a flange 34 formed such as to extend from an outer circumferential surface of the tubular part 33, and fins 35 formed to extend from the outer circumferential surface of the tubular part 33. The flange 34 is located substantially in the center of the lengthwise direction of the tubular part 33. The lower face of the flange 34 (lower left face in FIG. 5) is a flat surface. Six fins 35 are provided on the outer circumferential surface of the tubular part 33 at an interval of 60° such as to extend from the lower end (lower left end in FIG. 5) of the tubular part 33 to the lower face of the flange 34, their height from the outer circumferential surface of the tubular part being increased gradually.

In every other one of the regions between adjacent fins 35 on the outer circumferential surface of the tubular part 33 (divided into six regions) two each cleansing agent discharge ports 36 spaced apart from each other in the lengthwise direction of the tubular part 33 are formed. The lower end 33B of the tubular part 33 is closed by a dome-shaped dome part 37. Thus, the opening (cleansing agent injection port) at the upper end 33A of the tubular part 33 communicates with the cleansing agent discharge ports 36, so that, when a fluid is injected from the cleansing agent injection port, the fluid is discharged from the cleansing agent discharge ports 36. The distance from the lower face of the flange 34 to the top of the dome part 37 of this opener 30 is somewhat shorter than the depth of the navel cavity, and the size and the shape in the surface direction of the flange 34 are such that the flange can close the opening of the navel cavity and prevent the opener 30 to be inserted too far into the navel cavity. The size and the shape of the fins 35 are such that they can stretch and open a narrowing opening of the navel cavity gradually as the opener 30 is inserted, as will be described later.

The opener 30 thus structured can be used, for example, in the manner described below. First, the opener 30 is inserted into a navel cavity with a narrowing opening (not shown) from the side of the dome part 37 (lower end 33B) until the flange 34 abuts the surface of the belly near the navel cavity.

In this insertion process, the narrowing opening is pressed by the gradually enlarging peripheral parts of the fins 35 and gradually stretched and opened. In this state, the body cavity cleansing agent (fluid composition) of the present embodiment is injected from the cleansing agent injection port at the upper end 33A of the tubular part 33. As a result, the fluid composition is introduced into the navel cavity from the cleansing agent discharge ports 36 formed in the tubular part 33. The fluid composition is preferably introduced until the fluid composition makes sufficient contact with the tubular part 33 and the fins 35 inside the navel cavity.

After the lapse of a specified period time, the fluid composition has solidified and the solidified fluid composition (body cavity cleansing agent) is unified with the opener 30. Then, the tubular part 33 is picked to pull out the opener 30 from the navel cavity together with the body cavity cleansing agent. As a result, the bellybutton lint, together with the body cavity cleansing agent, is removed from the navel cavity, by this opener 30 as with the opener 3 shown in FIG. 2.

Also, with the opener 30, the opening of the navel cavity can be stretched and opened only by inserting the opener 30 into the navel cavity, and moreover, the fluid composition is efficiently introduced into the navel cavity by injecting it from the cleansing agent injection port with the opener 30 being inserted in the navel cavity. Accordingly, the processes of stretching and opening the navel cavity and injecting the fluid composition are easily performed as compared with the opener 3 shown in FIG. 2.

Figure 6:
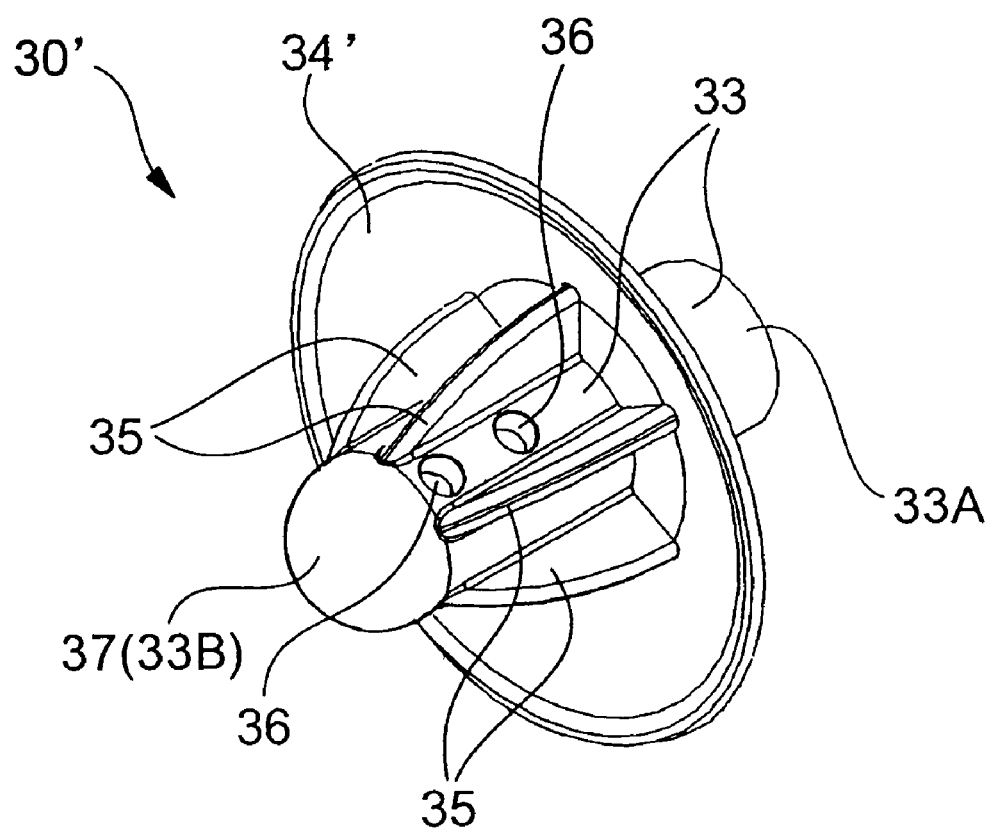
FIG. 6 is a perspective view showing another embodiment of the navel cavity opener of the present invention for stretching and opening the opening of a navel cavity.
Figure 7:
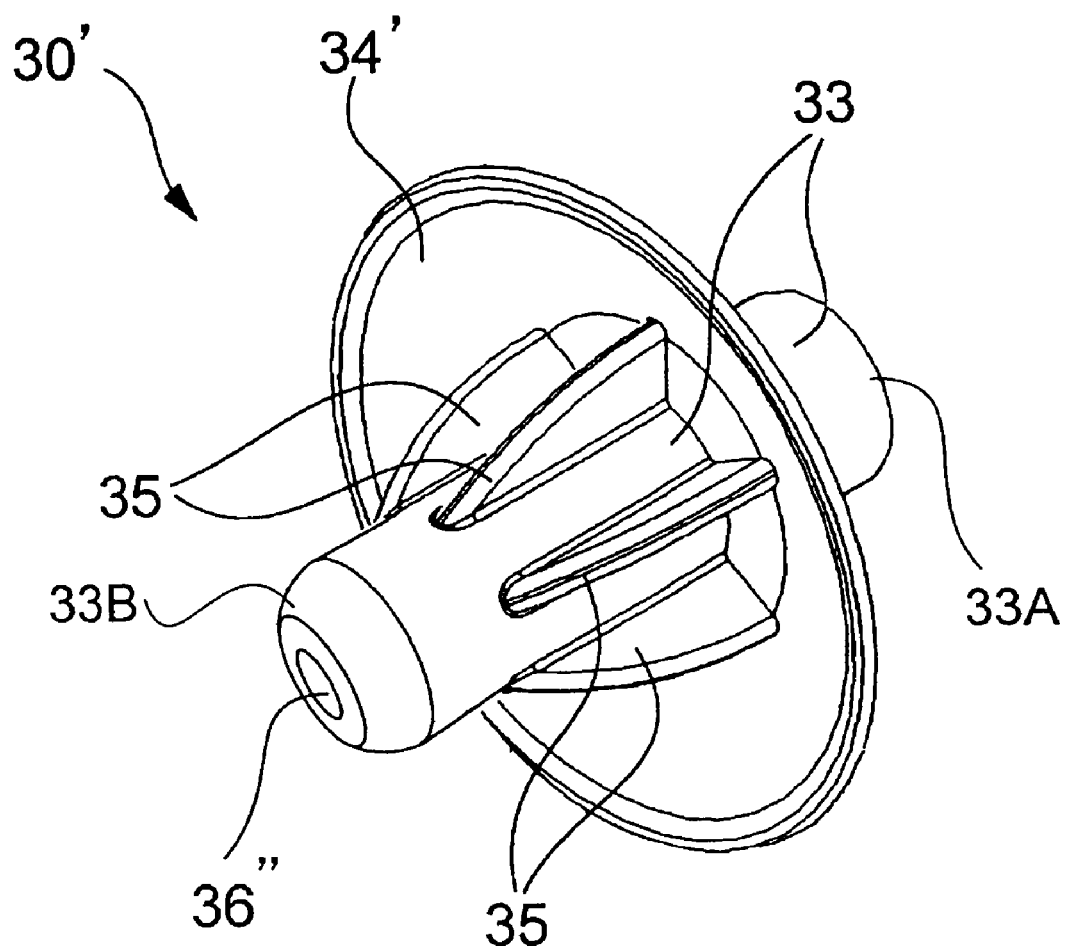
FIG. 7 is a perspective view showing a preferred embodiment of the navel cavity opener of the present invention for stretching and opening the opening of a navel cavity.

The opener 30' shown in FIG. 6 is a modified version in which the shape of the flange 34 of the opener 30 shown in FIG. 5 is changed. The opener 30' has the same structure as that of the opener 30 shown in FIG. 5 except that the flange 34' has a cup-like shape concaved from the lower end 33B side toward the upper end 33A side of the tubular part 33 (cup-like shape concaved relative to the lower end 33B of the tubular part 33). Therefore, the opener 30' shown in FIG. 6 can be used similarly to the opener 30 shown in FIG. 5. Further, with the opener 30' shown in FIG. 6, when the opener is inserted in the navel cavity and the fluid composition is injected, the peripheral part of the cup-like flange 34' presses down the belly surface near the opening of the navel cavity. Accordingly, the fluid composition introduced into the navel cavity is less likely to spill out of the navel cavity, as compared with the opener 30 shown in FIG. 5.

The opener 30" shown in FIG. 7 and FIG. 8(a) to FIG. 8(d) is a more preferred embodiment of the navel cavity opener of the present invention, in which the position of the cleansing agent discharge ports of the opener 30' shown in FIG. 6 is changed. More specifically, the opener 30" shown in FIG. 7 and FIG. 8(a) to FIG. 8(d) is a navel cavity opener for stretching and opening the opening of the navel cavity so that the body cavity cleansing agent can be poured into the navel cavity, similarly to the opener 30 shown in FIG. 5 and the opener 30' shown in FIG. 6. The opener 30" includes a tubular part 33, a flange 34' formed such as to extend from an outer circumferential surface of the tubular part 33, and a plurality of fins 35 arranged at a predetermined interval and extending from the outer circumferential surface of the tubular part 33. The tubular part 33 is provided with a cleansing agent injection port 38 at its upper end 33A, and a cleansing agent discharge port 36" that communicates with the cleansing agent injection port 38 on the lower end 33B side of the tubular part 33 relative to the flange 34'. The fins 35 are formed such as to extend from the lower end 33B of the tubular part 33 to the flange 34', their height from the tubular part 33 being increased gradually. The upper end 33A side of the tubular part 33 protrudes from the flange 34'.

Figure 8A:
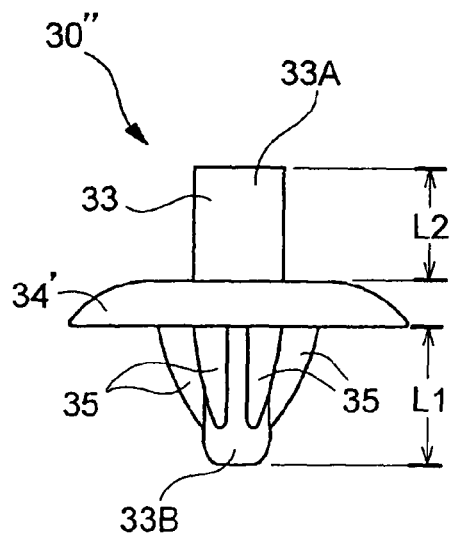
FIG. 8(a), FIG. 8(b), FIG. 8(c) and FIG. 8(d) are a front view, a plan view, a bottom plan view, and a cross section taken along the line D-D of FIG. 8(c), respectively, of the navel cavity opener shown in FIG. 7.
Figure 8B:
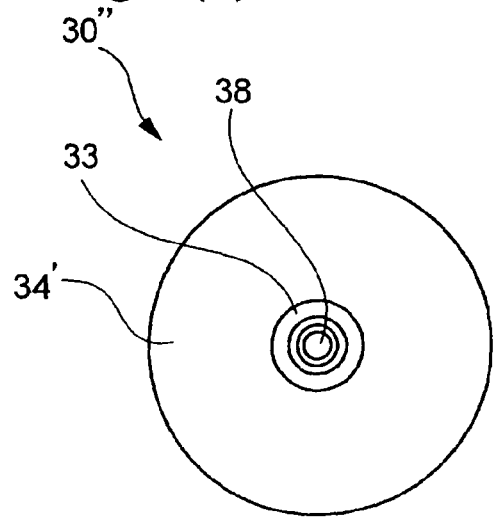
Figure 8C:
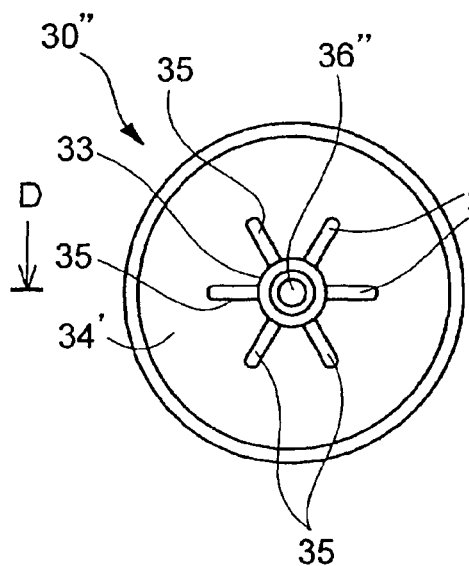
Figure 8D:
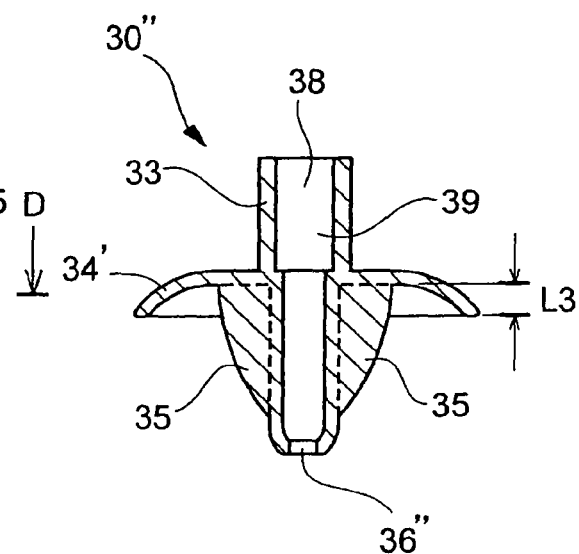

In this opener 30" shown in FIG. 7 and FIG. 8(a) to FIG. 8(d), as compared with the opener 30' shown in FIG. 6, the cleansing agent discharge port 36" is not provided on the outer circumferential surface of the tubular part 33, and instead in the lower end 33B of the tubular part 33. Therefore, as shown in FIG. 8(d), a cleansing agent conduit 39 is formed to communicate the cleansing agent injection port 38 at the upper end 33A and the cleansing agent discharge port 36" at the lower end 33B of the tubular part 33. Other features are the same as those of the opener 30' shown in FIG. 6.

The distance L1 (see FIG. 8(a)) between the lowermost end (peripheral part) of the flange 34' and the bottom end of the tubular part 33 is preferably somewhat shorter than the depth of the navel cavity, in particular, 10 to 15 mm. The distance L2 (see FIG. 8(a)) between the uppermost end of the flange 34' and the top end of the tubular part 33 preferably has a length that enables the user to readily hold the upper end 33A part above the flange 34' of the tubular part 33, in particular, 8 to 15 mm. The concave depth L3 of the cup-like flange 34' (distance between the lowermost end of the flange 34' and the deepest point of the concaved flange 34', as shown in FIG. 8(d)) is preferably deep enough to hold the fluid composition spilled out from the navel cavity when the fluid composition is poured into the navel cavity, in particular, 0 to 5 mm. The preferable ranges of the distance L1, the distance L2, and the concave depth L3 shall apply to other embodiments including the embodiment shown in FIG. 5 and the embodiment shown in FIG. 6.

With the opener 30" shown in FIG. 7 and FIG. 8(a) to FIG. 8(d), the opener 30" is inserted into a navel cavity (not shown) from the lower end 33B side of the tubular part 33 until the flange 34' abuts the belly surface near the navel cavity, and in this state, the body cavity cleansing agent (fluid composition) is injected from the cleansing agent injection port 38 of the tubular part 33, so that the fluid composition is introduced into the navel cavity from the cleansing agent discharge port 36" at the lower end 33B of the tubular part 33. The opener 30" shown in FIG. 7 and FIG. 8(a) to FIG. 8(d) can be used similarly to the opener 30' shown in FIG. 6 to achieve the same effects. Moreover, because the fluid composition is introduced into the navel cavity from the cleansing agent discharge port 36" at the lower end 33B of the tubular part 33, the fluid composition can readily reach the deepest part of the navel cavity, whereby bellybutton lint adhered to the deepest part of the navel cavity is readily removed.

Next, another preferred embodiment of the body cavity cleansing method of the present invention, in which the body cavity cleansing agent of the above embodiment is used for the cleansing of an ear hole (ear cleansing), i.e., the process steps for removing ear wax from an ear hole, will be described. First, an appropriate amount of the body cavity cleansing agent (fluid composition) is attached to the terminal end of a swab. The composition may be attached to the terminal end of a swab in an appropriate manner depending on the properties, the container shape, and the like of the composition. The terminal end of the swab is then inserted into the ear hole to apply the composition on the inner surface of the ear hole. When one application fails to provide a sufficient amount of the composition, this process is repeated. In this process, preferably, the composition is applied such as not to completely plug the ear hole.

After a sufficient amount of the composition has been applied to the ear hole, it is left standing for a specified period of time until the composition solidifies, with the swab used for the application being inserted in the ear hole. After the composition has solidified (cured), the swab is pulled out from the ear hole together with the solidified composition 1.

Figure 9:
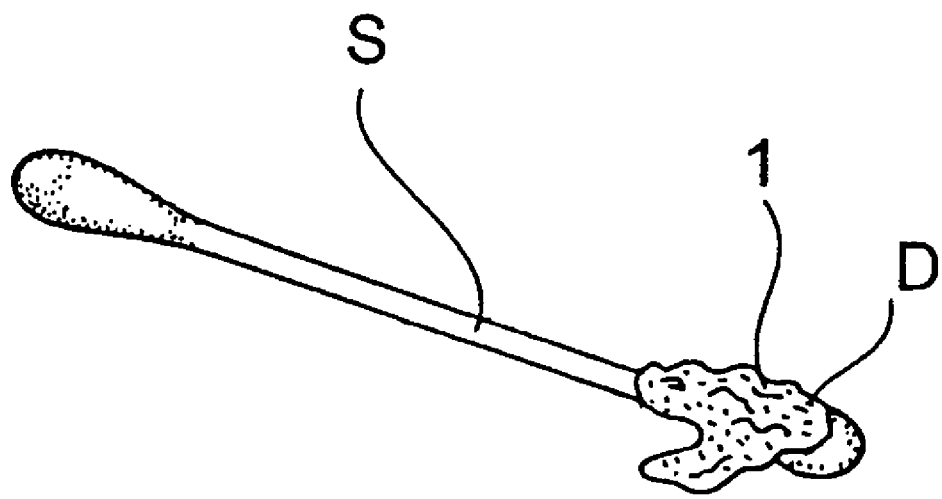
FIG. 9 is a perspective view showing a swab taken out of an ear hole with a solidified composition adhered to the swab.

As a result, as shown in FIG. 9, ear wax D is removed from the ear hole in a state that the ear wax D accompanies the composition 1 which is firmly attached to the terminal end of the swab S.

Thus, with the ear cleansing performed in the above embodiment using the body cavity cleansing agent 1 of the present embodiment and the swab S, the composition 1 is applied to the ear hole with the swab S and solidifies, after which the swab S is pulled out from the ear hole, whereby ear wax D is easily removed together with the composition 1. In this process, there is no risk of hurting the surface of the ear hole, as compared with scraping with an earpick or the like. Also, as with the bellybutton cleansing described above, it gives a feeling of the effect of the cleansing process.

The body cavity cleansing agent of the present invention is not limited to the above embodiment and may be variously modified within the scope of the present invention. Also, the body cavity cleansing agent of the present invention can be applied for purposes other than cleansing a navel cavity or an ear hole of a human body, such as cleansing of an ear hole (ear cleansing) of a pet animal or the like. That is, the body cavity cleansing agent of the present invention is applicable to a body of both a human and an animal. Further, the body cavity cleansing method of the present invention is not limited to the above embodiments and may be variously modified within the scope of the present invention. For example, the composition may be applied to the navel cavity, and various methods can be employed for the application. Alternatively, the composition may be poured into the ear hole, and various methods can be employed for the pouring.

In addition, the navel cavity opener of the present invention is not limited to the above embodiments and may be variously modified within the scope of the present invention. The shape of the tubular part can have other shapes than a cylinder, such as an oval cylinder, a hexagonal cylinder, or a square cylinder. The number of the fins may be other than six, for example, four or eight, depending on the size, depth, and the like of the navel cavity. The shape of the fins is not limited to that of the various embodiments described above, as long as the fins are formed such that the narrowing opening of the navel cavity can be stretched and opened gradually. The cleansing agent discharge port need not necessarily be located at the positions in the above embodiments, as long as it is provided on the lower end side of the tubular part relative to the flange. While the upper end 33A side of the tubular part 33 protrudes from the flange 34' in the above embodiments, other designs are possible, in which the tubular part does not protrude from the flange. The size of the flange in the surface direction in the above embodiments can be made smaller than the opening of the navel cavity. Further, other embodiments are possible wherein no flange is provided.

Example 1

The body cavity cleansing agent of this example is a two-component, condensation-hardening type silicone rubber composition including a first agent and a second agent at a weight ratio of 100:5, the first agent being a reactive silicone base with the following compositions, and the second agent being a curing agent base with the following compositions. This two-component, condensation-hardening type silicone rubber composition was accommodated in respective container parts of the container/injector case as shown in FIG. 1, to obtain a working product (example product 1).

Reactive silicone base (first agent): 100 weight parts (1) 65 weight parts of dimethylpolysiloxane terminated at both chain ends with hydroxyl groups, expressed by the following structural formula, and having a viscosity of 5100 mm$^2$/s at 23° C.:

Formula: $HO-Si(CH_3)_2-O-(Si(CH_3)_2O)_{450}-Si(CH_3)_2-OH$

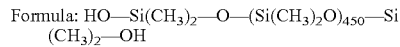

(2) 5 weight parts of fumed silica having a specific surface area of about 200 m$^2$/g (3) 30 weight parts of crystalline silica having an average particle size of 4.5 μm Curing agent base (second agent): 5 weight parts (4) 1.5 weight parts of dimethylpolysiloxane expressed by the following structural formula and having a viscosity of 100 mm$^2$/s at 23° C.:

Formula: $Si(CH_3)_3-O-(Si(CH_3)_2O)_{50}-Si(CH_3)_3$

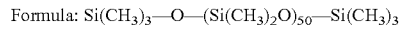

(5) 3 weight parts of methyl-trimethoxysilane (6) 0.5 weight parts of dibutyltin dilaurate

Example 2

The body cavity cleansing agent of this example is a two-component, addition reaction-hardening type silicone rubber composition including a first agent and a second agent at a weight ratio of 100:100, the first agent being a reactive silicone base with the following compositions, and the second agent being a curing agent base with the following compositions. This two-component, addition reaction-hardening type silicone rubber composition was accommodated in respective container parts of the container/injector case as shown in FIG. 1, to obtain a working product (example product 2).

Reactive silicone base (first agent): 100 weight parts (1) 64.8 weight parts of dimethylpolysiloxane terminated at both chain ends with vinyl groups, expressed by the following structural formula, and having a viscosity of 5000 mm$^2$/s at 23° C.:

Formula: $H_2C=CH-Si(CH_3)_2-O-(Si(CH_3)_2O)_{450}-Si(CH_3)_2-CH=CH_2$

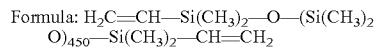

(2) 5 weight parts of fumed silica having a specific surface area of about 200 m$^2$/g (3) 30 weight parts of crystalline silica having an average particle size of 4.5 μm (4) 0.2 weight parts of 2% chloroplatinic acid solution in 2-ethyl hexanol Curing agent base (second agent): 100 weight parts (5) 60 weight parts of dimethylpolysiloxane terminated at both chain ends with vinyl groups expressed by the following structural formula and having a viscosity of 5000 mm$^2$/s at 23° C.:

Formula: $H_2C=CH-Si(CH_3)_2-O-(Si(CH_3)_2O)_{450}-Si(CH_3)_2-CH=CH_2$

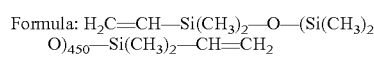

(6) 5 weight parts of fumed silica having a specific surface area of about 200 m$^2$/g (7) 30 weight parts of crystalline silica having an average particle size of 4.5 μm (8) 5 weight parts of hydrogen polysiloxane expressed by the following structural formula:

Formula: $Si(CH_3)_3-O-(Si(CH_3)_2O)_{50}-(Si(H)(CH_3)O)_{10}-Si(CH_3)_3$

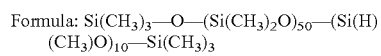

Example 3

Example 3 is the cleansing of a navel cavity using the above example product 1. The above example product 1 (container/injector case 2) in which the body cavity cleansing agent of the above example 1 is contained as shown in FIG. 1 was held by a hand, and as shown in FIG. 3(a) to FIG. 3(c), the partition 23 was crushed, so that the first agent 11 and the second agent 12 made contact with each other and were mixed together, to obtain the fluid composition 1 that can be poured into the navel cavity. Meanwhile, as shown in FIG. 4(a) and FIG. 4(b), the opening of the navel cavity N was stretched and opened using the opener 3.

Next, the fluid composition 1 in the container/injector case 2 was poured inside the stretched-open navel cavity N as shown in FIG. 4(c) and FIG. 4(d). In this state, after 10 minutes have passed, the fluid composition 1 solidified into a gel-like or rubber-like state. After that, this solidified material was pulled out from the navel cavity N together with the opener 3 as shown in FIG. 4(e). As a result, the bellybutton lint D adhered around the bottom of the navel cavity N was completely removed from the navel cavity N together with the body cavity cleansing agent 1, without hurting the inner surface of the navel cavity.

Example 4

Using the above example product 2, the navel cavity was cleaned similarly to the example 3. As a result, as with the example 3, the bellybutton lint D was completely removed from the navel cavity N. In this process, the time required for the fluid composition 1 to set into a gel form was about 1 minute.

INDUSTRIAL APPLICABILITY

With the body cavity cleansing agent and the body cavity cleansing method of the present invention, dirt such as bellybutton lint or ear wax and the like can be readily removed without hurting the inner surface of the navel cavity or the ear hole.

Further, with the navel cavity opener of the present invention, the opening of the navel cavity can be stretched and opened by just inserting the opener into the navel cavity. The body cavity cleansing agent can be efficiently introduced into the navel cavity simply by injecting the body cavity cleansing agent from the cleansing agent injection port of the navel cavity opener that is inserted in the navel cavity, and therefore the processes of stretching and opening the navel cavity and injecting the body cavity cleansing agent are performed simply.

The invention claimed is:

1. A navel cavity cleansing method comprising:
   opening a navel cavity,
   pouring or applying a navel cavity cleansing agent to the navel cavity, wherein the cleansing agent solidifies and takes a form that can be removed from said navel cavity together with dirt in the navel cavity; and
   removing the solid cleansing agent from the navel cavity together with dirt in said navel cavity;
   wherein the cleansing agent is a silicone rubber composition having two component hardening system comprising a first agent and a second agent, wherein said first agent comprises a reactive silicone base mainly composed of diorganopolysiloxane and the second agent comprises a crosslinking agent.

2. The navel cavity cleansing method according to claim 1, wherein said reactive silicone base and said crosslinking agent are either a combination of a hydroxylated diorganopolysiloxane comprising at least two hydroxyl groups in the molecule and an alkoxysilane comprising at least two alkoxy groups in the molecule, or a combination of a vinyl-terminated diorganopolysiloxane comprising at least two vinyl groups in the molecule and a hydrogenated diorganopolysiloxane comprising at least two Si—H groups in the molecule.

3. The navel cavity cleansing method according to claim 1, wherein the navel cavity is opened using a navel cavity opener comprising a tubular part, a flange formed such as to extend from an outer circumferential surface of said tubular part, and a plurality of fins provided at a predetermined interval extending from the outer circumferential surface of said tubular part, wherein:
   the tubular part is provided with a cleansing agent injection port at an upper end thereof;
   a cleansing agent discharge port that communicates with said cleansing agent injection port is provided on a lower end side of said tubular part relative to said flange; and
   said fins extend from the lower end of said tubular part toward said flange such that their height from said tubular part increases gradually.

4. The navel cavity cleansing method according to claim 3, wherein said cleansing agent discharge port is provided at a lower end part of said tubular part.

* * * * *